US006709681B2

(12) United States Patent
Benjamin et al.

(10) Patent No.: US 6,709,681 B2
(45) Date of Patent: *Mar. 23, 2004

(54) ACIDIFIED NITRITE AS AN ANTIMICROBIAL AGENT

(75) Inventors: Nigel Benjamin, London (GB); Hamish Dougall, Aberfeldy (GB); Anthony Ormerod, Aberdeen (GB)

(73) Assignee: Aberdeen University (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/330,654

(22) Filed: Jun. 11, 1999

(65) Prior Publication Data

US 2002/0136750 A1 Sep. 26, 2002

Related U.S. Application Data

(63) Continuation of application No. PCT/GB99/00605, filed on Mar. 1, 1999, which is a continuation-in-part of application No. 08/696,930, filed as application No. PCT/GB95/00338 on Feb. 17, 1995, now abandoned.

(51) Int. Cl.$^7$ ...................... A61K 33/00; A61K 31/375; A61K 31/19; A61K 31/194; A61K 31/21
(52) U.S. Cl. ...................... 424/718; 424/400; 424/408; 424/482; 514/474; 514/568; 514/557; 514/574; 514/858; 514/859; 514/865; 514/887; 514/931; 514/932; 514/933; 514/934; 422/29
(58) Field of Search ................................ 424/400, 408, 424/682, 718; 514/474, 568, 557, 574, 858, 859, 865, 887, 931–934; 422/29

(56) References Cited

U.S. PATENT DOCUMENTS

| | | | | |
|---|---|---|---|---|
| 65,174 | A | 5/1867 | Coffman | 424/75 |
| 206,343 | A | 6/1878 | McGowan et al. | 424/75 |
| 4,191,750 | A | 3/1980 | Hodosh | 424/127 |
| 4,595,591 | A | 6/1986 | Mardi et al. | 424/127 |
| 4,673,639 | A | 6/1987 | Slifkin | 435/36 |
| 4,923,899 | A | 5/1990 | Wachman et al. | 514/642 |
| 5,573,786 | A | 11/1996 | Grabo et al. | 424/718 |
| 5,595,101 | A | 1/1997 | Yoshimatsu et al. | 83/40 |
| 5,648,101 | A | 7/1997 | Tawashi | 424/718 |
| 6,103,275 | A | * 8/2000 | Seitz et al. | 424/718 |
| 6,190,704 | B1 | 2/2001 | Murrell | 424/718 |
| 2003/0175362 | A1 | * 9/2003 | Kross et al. | 424/718 |

FOREIGN PATENT DOCUMENTS

| | | |
|---|---|---|
| EP | 0 026 532 | 9/1980 |
| EP | 0 026 532 | 4/1981 |
| GB | 375738 | 2/1932 |
| JP | 59 085 278 | 5/1984 |
| JP | A 59 085 278 | 5/1984 |
| JP | A 62 142 559 | 6/1987 |
| SU | 229 744 A | 2/1969 |
| WO | WO 93/25213 | 12/1993 |
| WO | WO 95/22335 | 8/1995 |
| WO | WO 96/02268 | 2/1996 |

OTHER PUBLICATIONS

Derwent Abstract 1966–40545F, abstracting SU 229744, 1968.*
Block, Seymour S. Disinfection, Sterilization, and Preservation. 4th ed. Lea & Febiger, Philadelphia. pp. 818–819 and 60–61, 1991.*
Karupiah, et al., "Inhibition of Viral Replication by Interferon–y–Induced Nitric Oxide Synthase", 1993 Science 261:1445–1447.
Mannick, J.B., "The antiviral role of nitric oxide", 63rd Forum in Immunology, and papers in Intervirology 1995 38: 206–213.
Powell, et al., "The antiviral effects of nitric oxide", 1995 Trends in Mircrobiology; 3:81–82.
Mallinckrodt Baker, Inc., *Material Safety Data Sheet, Sodium Nitrite*, Phillipsburg, NJ.
Podstatova, G. et al., "Bactericidal and Corrosive Effect of Persteril with Anti Corrodible Agents", Biosis Abstract 180: 243396 (1980).
Weller, Richard et al., "A randomized trial of acidified nitrite cream in the treatment of tinea pedis" 1998, Department of Dermatology, Microbiology, and Medicine and Therapeutics, Aberdeen Royal Infirmary, Foresterhill, Aberdeen, United Kingdom.
Yoshida, et al., "Induction and Promotion of Forestomach Tumors by Sodium Nitrite in Combination with Ascorbic Acid or Sodium Ascorbate in Rats with or without N–Methyl–N'–Nitro–N–Nitrosoguanidine Pre–Treatment", *Int. J. Cancer*: 56,124–128 (1994).
Heaton, Charles L. et al., "The revival of nitric acid for the treatment of anogenital warts" 1993, Departments of Dermatology and Medicine, University of Cincinnati Medical Center, Cincinnati, and Solco Basle SA, Birsfelden, Cincinnati, OH.
Nesbitt et al., "Solubility Studies of Silver Sulfadiazine" *J Pharm Sci* 66 (4) 1977 CODEN: JPMSAE ISSN: 0022–3549 Biosis Abstract, Accession No. 77:190790 (1970).
K.D. Croen, "Evidence for an Antiviral Effect of Nitric Oxide," *The Journal of Clinical Investigation*, vol. 91, pp. 2446–2452 (1993).
G. Kurupiah et al., "Inhibition of Viral Replication by Interferon–gamma–Induced Nitric Oxide Synthase," *Science*, vol. 261, pp. 1445–1448 (1993).
K.L. Powell and S.A. Baylis,"Antiviral Effects of Nitric Oxide," *Trends in Microbiology*, vol. 3, pp. 81–82 (1995).

* cited by examiner

*Primary Examiner*—John Pak
(74) *Attorney, Agent, or Firm*—Fish & Richardson P.C.

(57) ABSTRACT

The present invention provides a dosage form for the treatment of bacterial, viral or fungal conditions which comprises, a pharmaceutically acceptable acidifying agent in an amount sufficient to reduce the pH at an environment of use to below pH4, and a pharmaceutically acceptable source of nitrite ions or a nitrate precursor therefor; wherein said acidifying agent and said source of nitrite ions or nitrate precursor are separately disposed in respective pharmaceutically acceptable carriers for admixture at the intended environment of use to release NO or $NO_2$ ions. The invention also provides delivery systems for the topical medicament.

27 Claims, 7 Drawing Sheets

ACIDIFIED NITRITE AS AN ANTIMICROBIAL AGENT

This application is a CIP under 35 U.S.C. §120 of U.S. patent application Ser. No. 08/696,930, filed Aug. 21, 1996 which is now abandoned, which was filed under 35 U.S.C. P.C.T. application Ser. No. PCT/GB95/00338, filed Feb. 17, 1995; and a continuation of 35 U.S.C. §371 to P.C.T. Application Ser. No. PCT/GB99/00605, filed Mar. 1, 1999, under 35 U.S.C. §119 to U.K. patent application Ser. No. 9403284.4, filed Feb. 21, 1994, under 35 U.S.C. §119 to U.K. patent application Ser. No. 9404365.0, filed Mar. 7, 1994, and under 35 U.S.C. §119 to U.K. patent application Ser. No. 98044696, filed Mar. 2, 1998.

The present invention relates in one aspect to acidified nitrite as an antimicrobial agent, and to a complex of nitrogen oxides arising from the interaction of nitrite and acid as an antiviral composition for the treatment of viral diseases of the skin by topical application thereto. Such nitrogen oxides include in particular NO which is of importance particularly if acidified.

An active entero-salivary circulation in man provides a continuous flow of nitrate into the mouth where it is rapidly reduced to nitrite by bacteria on the tongue. The effect of salivary nitrate excretion is to provide a precursor for the generation of nitrogen oxides by the break down of the nitrite.

In brief we have found that exposure of a yeast, *Candida albicans* and the bacterium *E coli* to concentrations of nitrite in saliva together with acid conditions similar to those found in the stomach for one hour caused a dose-dependent reduction in their survival. It is apparent therefore that the generation of nitrogen oxides and/or nitrous acid in the mouth and in the gastrointestinal tract, particularly the upper gastrointestinal tract, from acidified nitrite is preventative of microbial infection.

In the mouth bacteria rapidly reduce nitrates to nitrites. Once swallowed the acid conditions of the stomach protonate the nitrite to form nitrous acid (pKa approx 3.5). The nitrous acid in turn dissociates to form oxides of nitrogen as shown below.

$$NO_2^- + H+ = HNO_2 \tag{1}$$

$$2HNO_2 = H_2O + N_2O_3 \tag{2}$$

$$N_2O_3 = NO + NO_2 \tag{3}$$

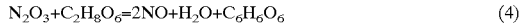

$$N_2O_3 + C_2H_8O_6 = 2NO + H_2O + C_6H_6O_6 \tag{4}$$

Endogenous and dietary nitrate is actively concentrated by salivary glands to more than 10 times the concentration in plasma and secreted in saliva. Thus the saliva provides a continuous source of nitrate to the upper gastrointestinal tract. Oral conversion of nitrate to nitrite is rapid and is restricted to the surface of the tongue in man and to the posterior third of the tongue in the rat.

The function of the entero-salivary circulation of nitrate is not known but it may well be that gastric acid by itself is not always sufficient to destroy many ingested micro-organisms and that the primary role of salivary nitrate secretion and conversion to nitrite is as a precursor for nitrogen oxides in the lumen of the stomach which will kill swallowed microorganisms.

The above identified mechanism is also applicable to the destruction of micro-organisms on an in the skin. For example athlete's foot or tidea pedis.

In WO 95/22335 we have disclosed a pharmaceutical composition comprising a pharmaceutically acceptable source of nitrites and a pharmaceutically acceptable acidifying agent, inter alia for the direct treatment of disease by topical application. These compounds have a direct effect on the organism concerned but the precise mode of action is not known.

U.S. Pat. No. 4,595,591 reveals a composition comprising an aqueous solution of nitric acid and nitrous acid at a pH below 1 preferably with a organic acid and copper and cadmium ions for the treatment of superficial lesion of the skin, for example tumorous growths.

U.S. Pat. No. 5,648,101 provides a vaso-active composition comprising NO adapted for delivery to a body site inter alia by means of a cream or ointment. The NO is generated from an admixture of ferrous sulphate, an organic acid and an inorganic nitrite and caused to be reactive in the presence of moisture adjacent or at the site. Acidification is not discussed.

WO 96/02268 reveals the inhibition of a virus by nitric oxide ($NO_2$) derived from a complex unstable organic molecule, but the advantages of reduction of pH at the environment of use have not been appreciated, neither have the beneficial effects the chemical release of the NO and $NO_2$ moieties immediately adjacent to the environment of use, been realized.

WO 93/25213 reveals a composition comprising nitrous oxide contained in a dermatological composition comprising as an essential feature a fatty acid or a lower alkyl ester thereof, pH values, particularly at the environment of use, are not mentioned.

All are single formulations which are admixed well prior to application to the environment of use so that NO and $NO_2$ all escape prior to use and hence have a very limited utility.

We have now found inter alia that nitrite at concentrations of up to 4% in an inert carrier cream or ointment when mixed with an organic acid such as salicylic acid reacts to produce oxides of nitrogen which are effective in killing infectious organisms on the skin including fungi, yeast, bacteria and viruses. The combination of nitrite and acid causes mild erythema (redness) of the skin due to release of nitric oxides at the environment of use but this causes no significant inflammation.

We have also found that as far as viruses, as opposed to bacteria for example, are concerned, that the above nitrogen oxide complex, comprising for example NO and/or $NO_2$ while it may effect replication to a degree, more importantly modifies the virally infected cells such that the immune system can recognize the viral particles. Inter alia, this is supported by the fact that the complex is less effective in immunosuppressed hosts. Generally the greater the percent of nitric oxide (NO) the better the immuno-potentiation. If possible up to 100% NO can be used.

It is thought, although more work is required, that smaller molecules, particularly NO and $NO_2$ penetrate the skin by direct diffusion or via the seat glands or hair follicles through the epidermis to the sweat cells. It has been found that although the healthy keratinocytes find the oxides of nitrogen toxic they do not die as they are relatively resistant to its effects. However, the surprising clinical results in our examples lead us to believe that virally infected cells are more susceptible to these effects, leading to destruction of the virally infected cells via a combination of toxicity leading to programmed cell death and potentiation of the immune response to the presence of the virus.

The above identified mechanism is also useful in the sterilisation of objects such as dentures by utilising a sterilizing nitrate solution. Conventional solutions which are effective in sterilising dentures often taste unpleasant due to chlorine-based disinfectants. A combination of nitrite and acid results in a antimicrobial solution which has little or no taste. Other objects such as contact lenses may be sterilised in the same way.

Gastroenteritis continues to be a major problem in rearing pigs and other farm animals. Enteropathogenic *Escherichia coli* (especially those bearing the K88 antigen) are particularly implicated. Although gastric acidity is thought to be one of the main host defence systems which provides a barrier to orally-acquired infection, this is clearly ineffective in preventing organisms from reaching the more distal intestine in these animals.

The role of NO as a compound which inhibits viral replication in vitro has been disclosed by J. B. Mannick; $63^{rd}$ Forum in Immunology, and papers in Intervirology 1995; 38: 206–213, Trends in Microbiology 1995; 3: 81–82, Science 1993; 261: 1445–1448, and The Journal of Clinical Investigation 1993; 91: 2446–2452. The above papers disclose the effects of NO on various viruses, for example herpes simplex virus, vaccinia virus and vesicular stomatitis virus. Exogenous NO donors such as S-nitroso-N-acetyl penicillamine(SNAP)or SIN-1 were used in vitro to determine the role of NO as an antiviral compound. Application of exogenous NO to cell-lines infected with the virus under test resulted in inhibition of the viral DNA replication. The exact mechanism of the inhibition seemed to differ depending on the virus involved. For example in the case of vaccinia virus it is thought that the NO may inhibit replication by binding to non-haem iron or thiol groups that are essential for the catalytic activity of enzymes involved in vaccinia replication. In this in vitro model the antiviral effects of NO do not require immune recognition of infected cells thus providing an early defence against viral pathogens prior to the development of a specific immune response.

In order for viruses to survive and reproduce they must evade recognition by the hosts immune responses. The mechanism by which this is achieved is largely unknown but an effective immune response eradicates the infection. Viruses are obligate intracellular pathogens. They reproduce using the host's metabolic machinery.

At present drug treatment of viral diseases is predicted upon a small number of compounds which block the replication of the virus. For example Acyclovir, which is effective against herpes virus, is a deoxyguanosine analogue which competes with deoxyguanosine triphosphate as a substrate for viral thymidine kinase and when phosphorylated and incorporated in the viral DNA causes premature DNA chain termination.

Unfortunately anti-viral drugs are only effective for a limited number of viral infections and viruses can mutate to overcome the effectiveness of the drugs. In the case of molluscum contagiosum 1 and 2, which are related to orthopox and parapox viruses and share some homology with vaccinia, other forms of treatment have to be used. Current therapies comprise physical destruction with manual extrusion, liquid nitrogen therapy or curettage, all of which are painful and not very effective and may cause scarring. The pain of these therapies is particularly pertinent because the majority of patients are under the age of 10 years.

In the case of recalcitrant warts, destructive therapies such as liquid nitrogen can be used in cases where the conventional salicylic acid paints have not resulted in the warts disappearance. One problem with warts is that the viral pool is in the stem cells which are found at the base of the epidermis. The aforementioned treatments often remove the virus particles and thus the infection from the top layer of the epidermis, but they do not penetrate deep enough to remove the stem cells and therefore the origins of the infection. This can result in the re-emergence of the warts.

An alternative treatment for warts is by use of dinitrochlorobenzene. Such treatment is intended to make the patient allergic to dinitrochlorobenzene, whereupon the patient's immune system mounts an immune response to the dinitrochlorobenzene at the site of the wart and the wart in some cases disappears, presumably as a result of immuno-potentiation. Immuno-potentiation can be an effective treatment but subjecting the patient to an allergic reaction caused by dinitrochlorobenzene can be hazardous, variable and difficult to control.

According therefore to a first aspect of the present invention there is provided a dosage form for the treatment of bacterial, virus, or fungal conditions in the human or animal body which comprises:

a pharmaceutically acceptable acidifying agent in an amount sufficient to reduce the pH at an environment of use to below pH4, and a pharmaceutically acceptable source of nitrite ions or a nitrate precursor therefor;

wherein said acidifying agent and said source of nitrite ions or nitrate precursor are separately disposed in respective pharmaceutically acceptable carriers for admixture at the intended environment of use to release NO or $NO_2$ ions.

Preferably the acidifying agent is an organic acid, for example salicylic acid or ascorbic acid. The precursor for the $NO_2$ or NO moiety may be an alkaline metal or alkaline earth metal nitrate capable of conversion to $NO_2$ or NO by enzymic action.

The pharmaceutical acceptable carrier or diluent may be an inert cream or ointment. In a particularly preferred form of the invention the acidifying agent and the source of nitrite ions or precursor therefor are separately disposed in said cream or ointment for admixture to release $NO_2$ or NO ions at the environment of use. Alternatively an acid composition may be presented for administration in tablet or liquid form.

Depending on the type of viral infection the components of the nitrogen oxide can work synergistically or alone. Nitrogen oxides, for example NO and $NO_2$, particularly can diffuse through the epidermis. In the case of warts this allows them to reach the stem cells which are at the base of the epidermis and are the cells which contain the pool of established virus. Once at the infected cells the nitrogen oxide complex can facilitate programmed cell death, selectively in infected cells, which may then be taken up by phagocytes and antigen presenting calls leading to immune recognition of the previously hidden viral antigens. Once recognized, specific immunity will lead to destruction of all infected cells through cellular and humoural responses.

Accordingly therefore to a further aspect of this invention there is provided a method of exposing virally infected cells at or adjacent an environment of use to a mammalian immune response in vivo, which comprises applying to said cells an admixture of nitrogen oxides generated by admixing at the environment of use a pharmaceutically acceptable acidifying agent in an amount sufficient to reduce the pH at the environment of use to below pH4 and a pharmaceutically acceptable source of nitrogen oxides or a nitrate precursor therefor.

According to a second aspect of the invention there is provided the use in the manufacture of a topical medicament for the in vivo potentiation of the immune system during a viral skin infection resultant from virus replication in the epidermis, of topical formulations comprising a separately disposed source of pharmaceutically acceptable nitrogen oxides, and a separately disposed pharmaceutically acceptable acidifying agent, for admixture, at an intended environment of use to release NO and $NO_2$ moieties.

Preferably the viruses replicating in the epidermis which cause the viral skin infection are selected from molluscum contagiosum, herpes simplex type 1 and 2, varicella zoster virus and papilloma virus. Treatment using the acidified nitrogen oxide source has been shown to be particularly effective in viral skin infections caused by the aforementioned viruses.

Conveniently the source of nitrogen oxides contains nitric oxide and may also contain NO- or NO+ nitrosium ions or a precursor therefor produced when a pharmaceutically acceptable acidifying agent and a pharmaceutically acceptable donor of nitrogen oxides or a precursor therefor, are brought into intimate contact at a site of biological action (environment of use).

If the pharmaceutically acceptable acidifying agent and the pharmaceutically acceptable donor of nitrogen oxides, or a precursor therefor were brought into contact before reaching the site of biological action the efficacy of the treatment is diminished as the nitrogen oxides become progressively more inactive with time.

In a preferred embodiment the pharmaceutically acceptable acidifying agent, the pharmaceutically acceptable donor nitrogen oxides or a precursor therefor are each separately disposed in a pharmaceutically acceptable carrier or diluent.

Preferably the pharmaceutically acceptable acidifying agent is an organic acid or salt with a low pH such as ascorbyl palmitate. The organic acid may be selected from at least one of ascorbic acid, ascorbyl palmitate, salicylic acid, lactic acid, citric acid, formic acid, benzoic acid and tartaric acid.

The choice of acidifying agent depends on the type of infection of the skin and the reaction of the infected areas to treatment. The use of reducing acids such as ascorbic acid gives a quick burst of NO and $NO_2$ with significantly more NO produced compared to the amount of $NO_2$ produced. The other organic acids such as salicylic acid give a sustained concentration of NO and $NO_2$ over a certain time period wherein the ratio of NO to $NO_2$ is low. The concentration of the inorganic nitrite, for example sodium nitrite (or other alkali metal nitrites), as the pharmaceutically acceptable donor of nitrogen oxides or a precursor therefor depends on the acid used and the concentration of the acid used. The reducing acid ascorbic acid is highly reactive so therefore only between 1–10% is required with stoichiometric concentrations of the pharmaceutically acceptable donor of nitrogen oxides or a precursor therefor (e.g. sodium or other alkali metal nitrite). Ascorbyl palmitate is more stable but requires a higher concentration than ascorbic acid because the palmitate has a higher molecular weight. A concentration of between 3% and 25% of ascorbyl palmitate is thus required. If salicylic acid is used, concentrations of between 0.5% and 30% are appropriate, citric acid requires a yet higher concentration of up to 45%. (All % given herein are by weight).

The concentration of sodium nitrite required to react with the above mentioned concentrations of organic acid is between 0.5% and 30%, preferably between 5% and 20%. Other pharmaceutically acceptable sources of nitrogen oxides or a precursor therefor require different ranges of concentration.

Preferably the pharmaceutically acceptable acidifying agent and the pharmaceutically acceptable donor of nitrogen oxides or a precursor therefor are in stoichiometric concentrations. If the pharmaceutically acceptable acidifying agent and the pharmaceutically acceptable donor of nitrogen oxides or a precursor therefor are in stoichiometric concentrations, after the reaction is completed there will be no unreacted compounds left. Accordingly any compounds remaining on the infected area will not be able to contaminate healthy skin with the active medicament or anything the treated area touches such as furniture and clothing.

In a preferred embodiment the medicament is in the form of a paint, a varnish, an ointment, a wax, a salve, or a cream. These embodiments allow the pharmaceutically acceptable acidifying agent and a pharmaceutically acceptable donor of nitrogen oxides, or a precursor therefor to be applied directly to the infected area. The treatment comprising the topical application of separate compositions according to this invention is preferably continued for at least one month, and more preferably two months.

In a further aspect of the present invention there is provided a two-part delivery system for the topical application of a medicament for the in vivo treatment of the epidermis, the said system comprising separately;

a first waxy component comprising a pharmaceutically acceptable acidifying agent;

and a second waxy component comprising a pharmaceutically acceptable source of nitrogen oxides whereby if topically applied in vivo simultaneously, or immediately sequentially, to the environment of use, active nitrogen oxides are released therefrom.

In a further embodiment, the first and second waxy components comprise a paraffin. The acidifying agent is preferably a reducing organic acid or salt such as ascorbic acid or ascorbyl palmitate. The source of nitrogen oxides may be an alkali metal nitrite such as sodium nitrite.

The use of a reducing acid or salt thereof results in a product released at the environment of use which comprises a major amount of NO which has significant therapeutic and immunological effects.

Thus the invention provides for the use of a source of oxide(s) of nitrogen in the manufacture of a composition for the treatment or prophylaxis of a viral skin infection by a virus selected from herpes simplex types 1 and 2, varicella zoster, vaccinia or papilloma, and particularly from molluscum contagiosum.

In a further aspect of the invention there is provided a delivery system for the topical application of a medicament for the in vivo treatment of the epidermis, comprising an adhesive layer and a support layer impregnated with at least one of the components of the medicament, characterized in that the components of the medicament are a pharmaceutically acceptable acidifying agent and a pharmaceutically acceptable donor of nitrogen oxides or a precursor therefor, and a means of combining the pharmaceutically acceptable acidifying agent with the donor of nitrogen oxides. For example the delivery system may comprise two layers, which when in situ release the oxides of nitrogen including nitric oxide. The activation can be by pressure applied or by hydration from the skin.

Preferably the delivery system is adapted for the potentiation of the immune system during a viral skin infection resultant from virus replication with the delivery system in place, such a system may, for example, resemble an adhesive plaster so it is then simple to apply physical pressure to the exterior of the plaster.

Conveniently the donor of pharmaceutically acceptable nitrogen oxides may be aqueous and encapsulated in microspheres or liposomes disposed in the support, preferably in the form of a film or a gauze. The film or gauze allows increased concentrations of the pharmaceutically acceptable acidifying agent to be used. If a solution of salicylic acid is used then only a concentration of 20–26% by weight is applied, but if salicylic acid is impregnated in the film or the gauze then a concentration of 26 to 44% by weight can be applied.

A further advantage of using an adhesive layer is that it can be used to occlude the infected area during treatment which increases the concentration of nitrogen oxides being absorbed through the epidermis.

Another advantage of using the delivery system as just described, instead of two creams or ointments, is that the components of the medicament will only be applied to the infected site, i.e. no spillage will occur. It is also easier for the elderly, who may have shaky hands, to apply the adhesive layer rather than applying a paint. For the treatment of molluscum contagiosum, which is mainly found in those under the age of 10 years, the adhesive layer can be a decoratively patterned in order to appeal to children.

As stated above preferably the integrity of the vehicle is disrupted by pressure after application of the adhesive layer and film or gauze to a site of viral infected skin. If the pharmaceutically acceptable acidifying agent and the pharmaceutically acceptable nitrogen oxide donors or precursors therefor are not kept separate until administration at the site of biological action they will react together thus rendering the medicament less effective. Accordingly, in this embodiment it is necessary for the pharmaceutically acceptable acidifying agent and the pharmaceutically acceptable nitrites or precursors therefor to be retained separately within the film or gauze layer. The application to the site of biological action of pressure applied to the adhesive layer, and therefore the film or gauze layer, can result in the vehicles, such as the microspheres or lipsomes, breaking and the pharmaceutically acceptable acidifying agent and the pharmaceutically acceptable nitrogen oxide donors or precursors therefor reacting, thus treating the infected area.

In another aspect the delivery system may be used in conjunction with a topically applied medicament. The topically applied medicament being either a pharmaceutically acceptable acidifying agent or a pharmaceutically acceptable donor of nitrogen oxides or a precursor therefor.

It is thus possible to provide only one of either the pharmaceutically acceptable acidifying agent or the pharmaceutically acceptable nitrogen oxide donors or precursors therefor impregnated in the film or gauze layer. The other compound, which is not impregnated in the film or gauze can then be applied topically to the infected site. The advantage of this arrangement is that the film or gauze layer can be larger than the infected site but a reaction between the pharmaceutically acceptable acidifying agent and the pharmaceutically acceptable nitrogen oxide donors or precursors therefor only occurs at the infected site where the medicament had been topically applied.

It is also possible to vary the treatment regime by changing the topically applied medicament without changing the compound in the delivery system. For example if the pharmaceutically acceptable nitrogen oxide donors or precursors therefor are impregnated in the film or gauze, then the type of pharmaceutically acceptable acidifying agent that is topically applied can be altered and the same adhesive and film or gauze layers utilized.

The delivery system is an ideal form of treatment for the verrucae on the feet because the delivery system is hidden from view.

In a further aspect of the invention there is provided a method of sterilising an object which method comprises the steps of:

1) preparing a pharmaceutically acceptable acidifying agent and a pharmaceutically acceptable source of nitrite ions, 2) mixing said acidifying agent with said source of nitrite ions in a liquid carrier or diluent in contact with said object thereby to reduce the pH to below 4 while causing said steriliant nitrite ions to sterilize said object.

In a further form of the invention there is provided a sterilant composition comprising a pharmaceutically acceptable acidifying agent, a pharmaceutically acceptable source of nitrite ions or a nitrate precursor therefor, and a pharmaceutically acceptable carrier or diluent therefor wherein the acidifying agent is adapted to reduce the pH at the environment of use to below pH4.

In a still further form of the invention there is provided an animal feed supplement comprising a pharmaceutically acceptable acidifying agent and, a pharmaceutically acceptable source of nitrite ions or a nitrate precursor therefor or, in an amount sufficient to produce a beneficial anti-microbial pharmalogical effect, but insufficient to produce adverse action in the target animal.

The acidifying agent may be salicylic or ascorbic acid as above, and the source of nitrite ions or nitrate precursor therefor may be in an inorganic nitrate as set forth above. Where the animal is the pig, the supplement should be included in an amount sufficient to ensure that each adult animal will receive a balanced dose of between 0.3 to 5.0 g/day and preferably about 1 g/day.

The invention will now be described, by way of illustration only, with reference to the following examples and figures accompanying the specification.

BREIF DESCRIPTION OF THE DRAWINGS

Figure 4:
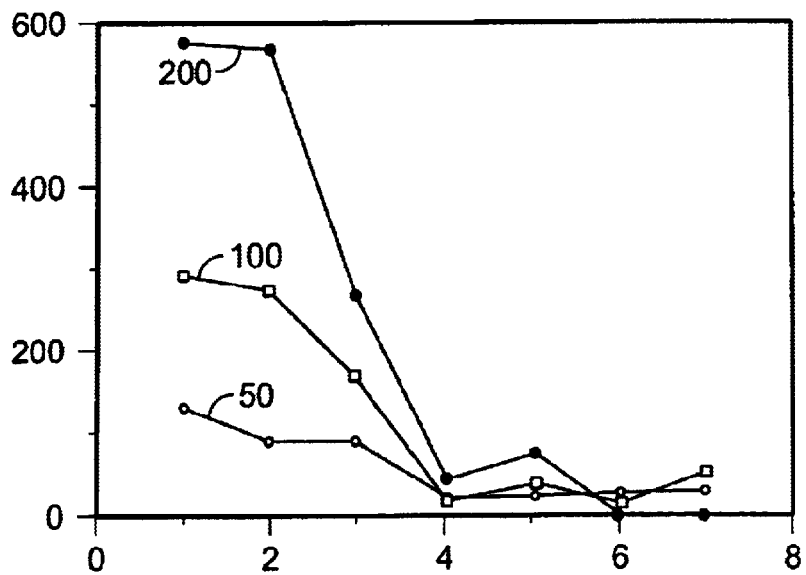
FIG. 4 shows the generation of nitric oxide from sodium nitrite at different levels of acidity where the vertical axis is the nitric oxide concentration (nM) and the horizontal axis is Ph.
Figure 7:
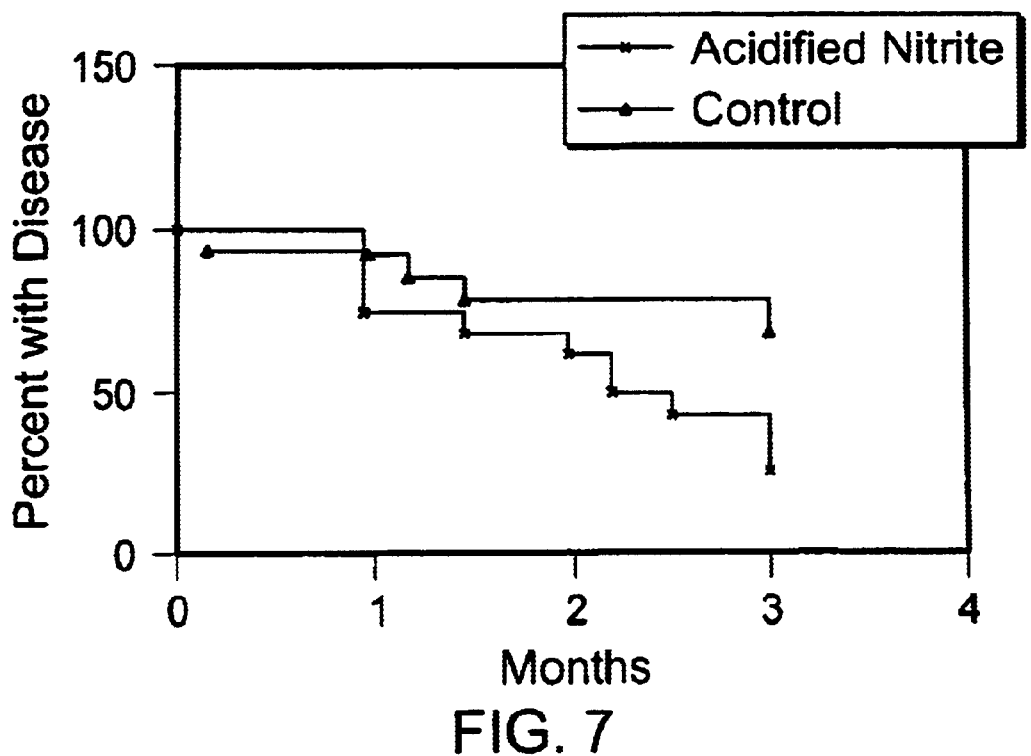
Figure 8:
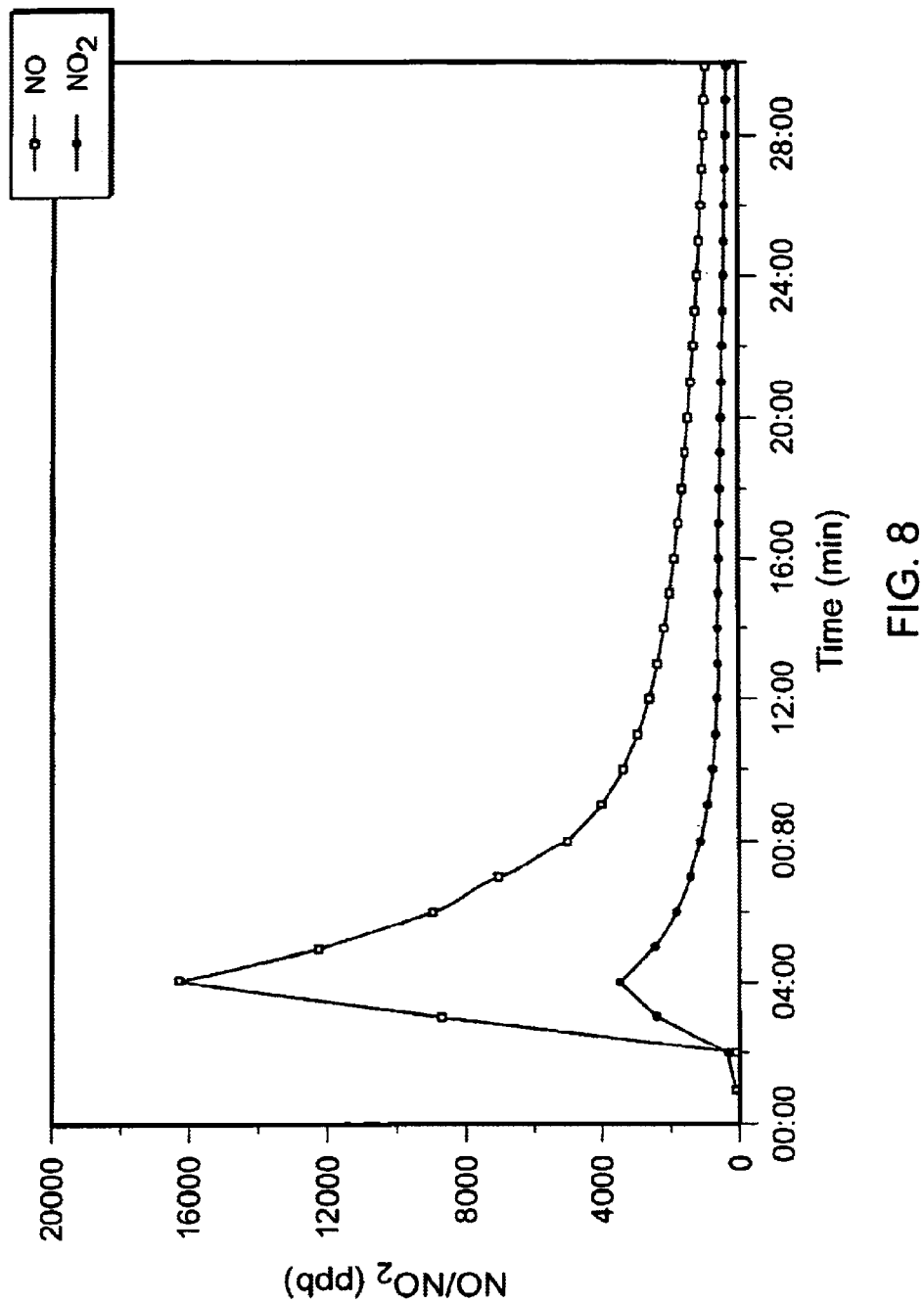

FIG. 7 shows a Kaplan Meier plot of the outcome of the treatment of patients with molluscum contagiosum as a function of time; and FIG. 8 shows a graph of NO and NO2 release from 0.083 g of 10% Ap wax with 0.014 g of 10% sodium nitrite wax to give 21$\mu$ moles of $NaNO_2$ and 25$\mu$ moles of ascorbyl palmitate. In FIG. 4 the curve with "squares" denotes NO values whereas the curve with "circles" denotes $NO_2$ values.

EXAMPLE 1

Figure 1:
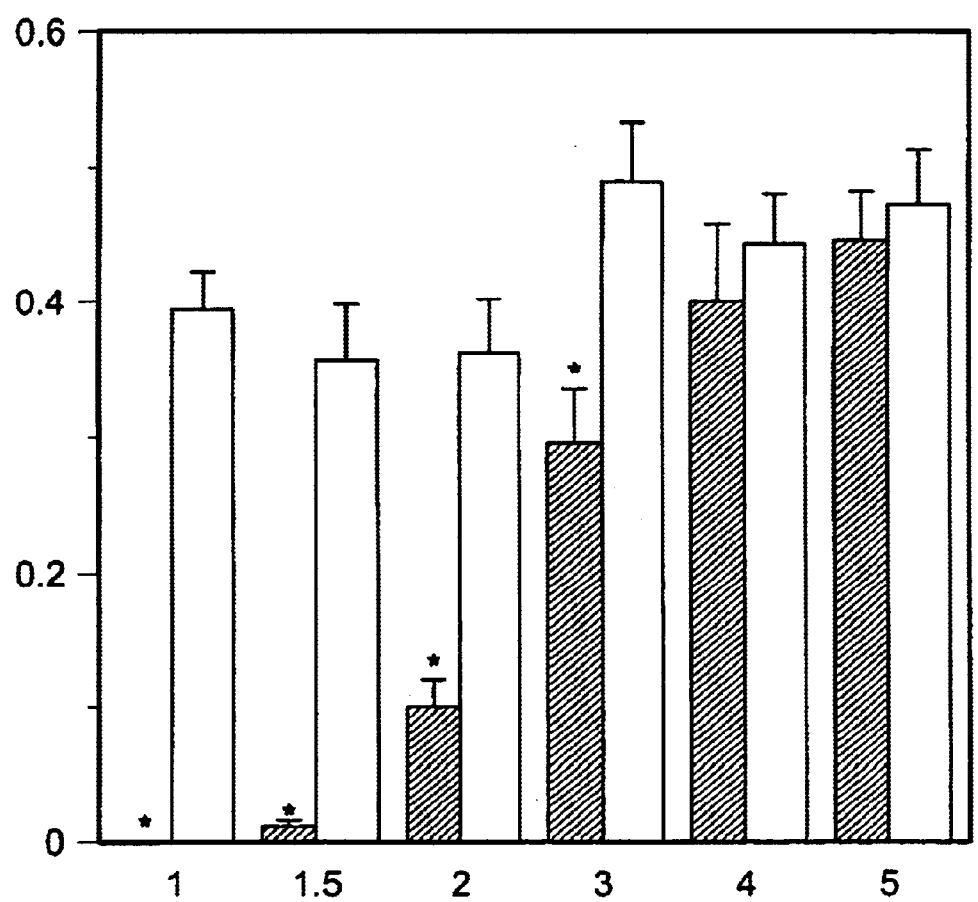
FIG. 1 shows a diagram indicative of the effect of exposure to nitrate and differing hydrogen ion concentrations on the survival of $C$ $albicans$ where the vertical axis is the optical density in absorbance units and the horizontal axis is the pH.

With reference to FIG. 1 a single colony of *C albicans* was used to inoculate an overnight culture in Sabouraud's broth. 10 µl of this broth was added to 940 µl of a citrate/phosphate buffered Sabouraud's broth to which was added sodium nitrite (50 µl; final concentration 250 µM) or distilled water as a control. After one hour incubation at 37° C., 10 µl was removed and cultured in 190 µl standard Sabourauds broth with continual agitation (Gallenkamp orbital incubator) in a 96-well microtitre plate at 37° C. Growth was monitored by measurement of optical density at 570 nm at regular time intervals. The results are a mean of 16 separate experiments.

The effect of exposure to nitrite and differing hydrogen ion concentrations on the survival of *C albicans* is shown in FIG. 1. The open bars show the growth of *C albicans* measured by the optical density method following exposure to acid alone for 1 hour, while the closed bars show growth following exposure to acid and 250 µM sodium nitrite. There is a significant difference from the control at p>0.05 (Mann-Whitney U test). It is apparent therefore that the incubation of *C albicans* in acid alone for one hour had little effect on the number of viable organisms subsequently grown, whereas in contrast the addition of sodium nitrite at 250 µgM incrementally killed *C albicans* as the pH was reduced to below 4. The nitrite was in fact effective in eliminating *C albicans* at pH 1 at all concentrations above 250 µM (data not shown). 5 nN nitrite killed *C albicans* at up to pH5. It is significant that a random sample of 10 laboratory personnel on a normal diet had fasting salivary nitrite which varied from 23 to 220 µM (mean 114 µM) rising to 409 to 1890 µM (mean 1030) 45 minutes after ingestion of 200 mg potassium nitrate solution.

EXAMPLE 2

Figure 2A:
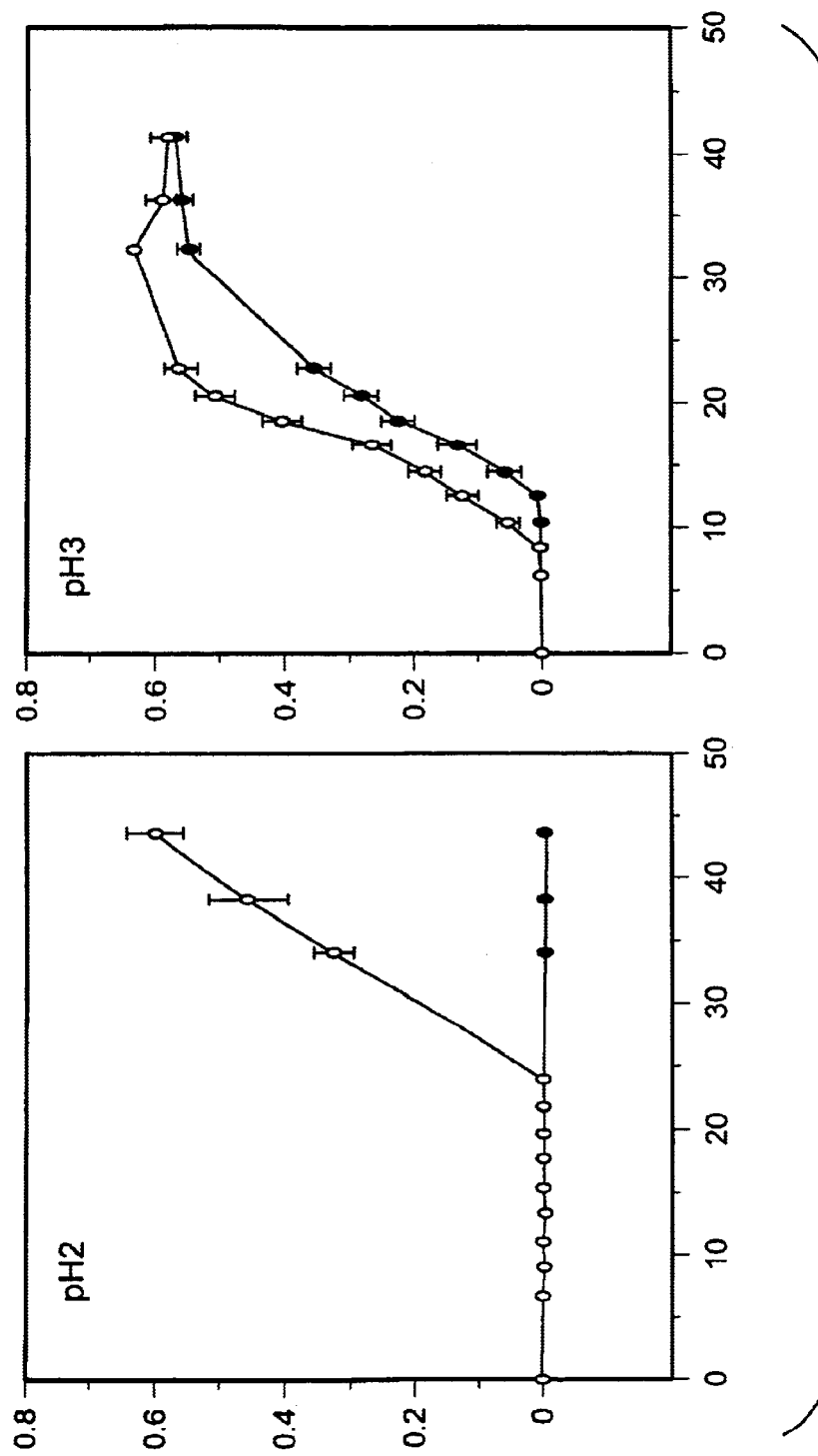
FIGS. 2A and 2B show growth curves of $E$ $coli$ following exposure to acid alone or acid with a nitrite where the vertical axes are optical density in absorbance units and the horizontal axes are time in hours.
Figure 2B:
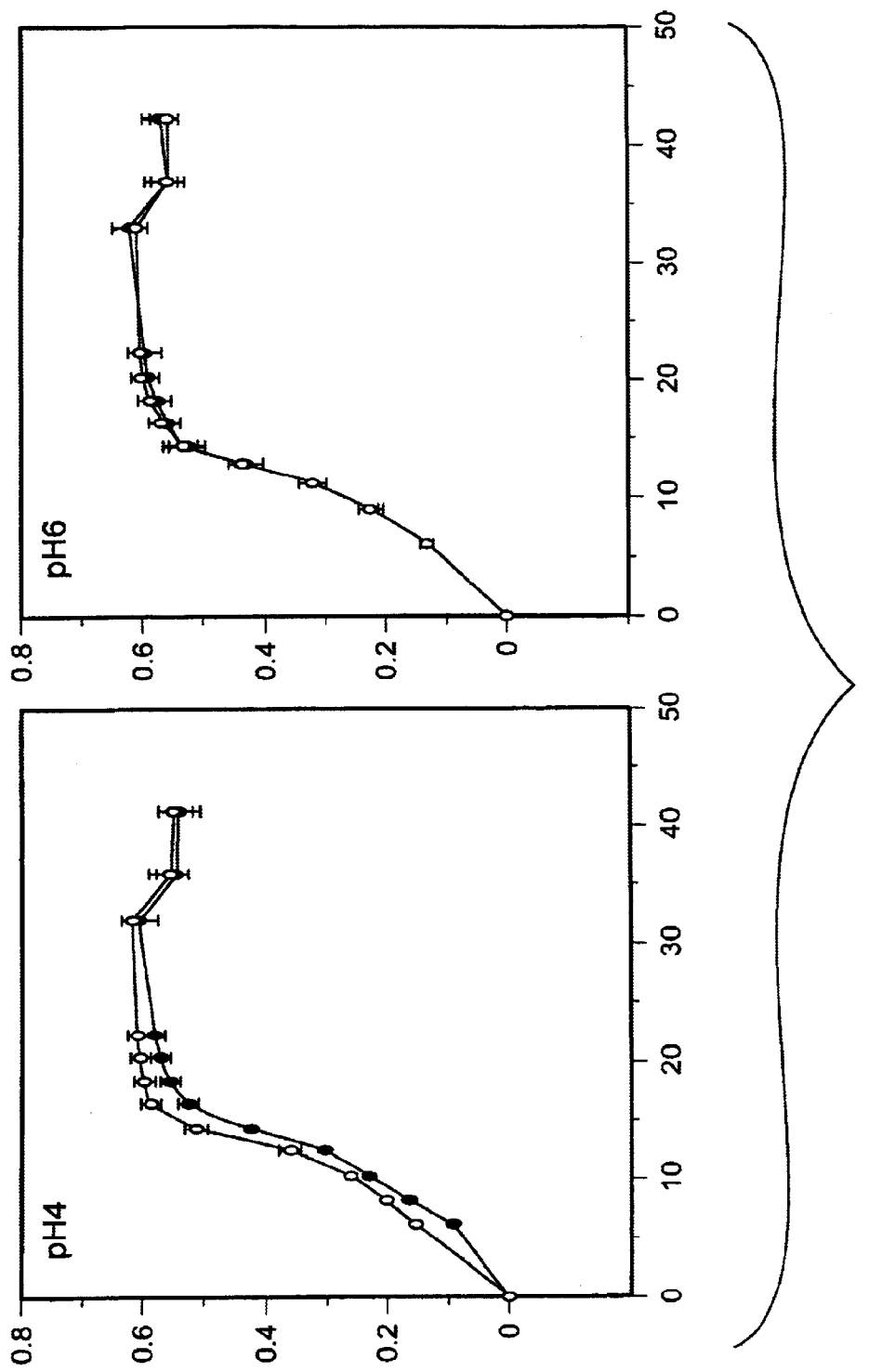

FIGS. 2A and 2B show growth curves of *E coli* following exposure to acid alone (open symbols) or acid and 250 µM nitrite (closed symbols). Growth was significantly (p<0.05) impaired at pH 2, 3 and 4 in the presence of nitrite compared with control.

The same methods were used as in FIG. 1 except *E coli* (strain NCTC 10418 grown on MacConkey's agar) was used and nutrient both (Oxoid CM1) was used in place of Sabouraud's broth. The results shown in FIGS. 2A and 2B are a mean of 20 experiments. As can be seen from FIGS. 2A and 2B *E coli* is more susceptible to acid than *C albicans*. Nevertheless exposure to pH 2 for one hour does not kill all the organisms as there is significant growth in the nutrient broth. At pH3 many more organisms survive. The addition of 250 µM nitrite to the exposure medium eliminates *E coli* at pH2 and significantly reduces the viability of this organism at pH3 and pH4. Nitrite at this concentration had no effect above pH4.

EXAMPLE 3

Figure 3:
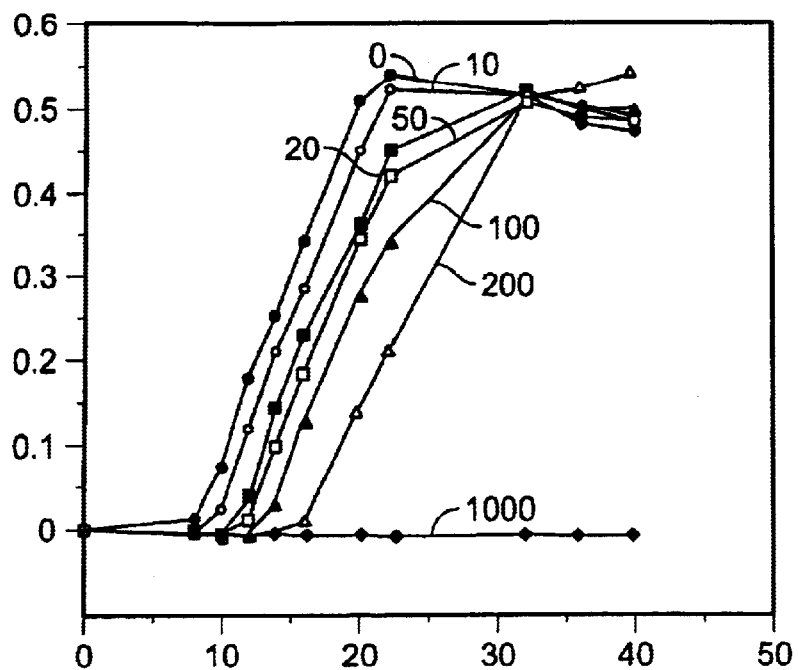
FIG. 3 shows growth curves of $E$ $coli$ following exposure to pH3 in various nitrite concentrations where the vertical axis shows the optical density in absorbance units and the horizontal axis is time in hours.

FIG. 3 shows growth curves of *E coli* following exposure to pH3 in various nitrite concentrations (10–1000 µM final concentration). The methods are those as for FIG. 2. FIG. 3 shows that there is a direct relationship between the toxic effects of nitrite on *E coli* and nitrate concentration at pH3. Even 10 µM had a discernable effect whereas 1 mM killed *E coli* completely.

EXAMPLE 4

FIG. 4 shows the generation of nitric oxide from sodium nitrite (as µM) at different acidities. Conditions were the same as those used for the exposure of organisms in FIG. 1. In particular nitrite was added to citrate/phosphate buffer to achieve final concentrations shown in FIG. 4. Nitric oxide concentrations in the buffer were measured by a nitric oxide sensitive meter (ISO-NO, World Precision Instruments) connected to a Maclab acquisition system and Macintosh computer. Measurements were recorded continually and readings were taken at 2 minutes when nitric oxide concentration had reached a steady state. FIG. 4 shows the release of nitric oxide as a result of reducing pH. Nitric oxide, which we have shown is generated under experimental conditions in FIG. 4 readily diffuses through cell membranes and has a high affinity for iron-sulphur containing respiratory enzymes and damages bacterial DNA. When produced enzymatically by activated leucocytes, nitric acid will kill Leishmania sp., Staphylococcus sp., Francisella sp. and Microbacterium as well as *C albicans*. Reaction with superoxide under acid conditions may additionally produce highly reactive hydroxyl radicals.

EXAMPLE 5

In a study to investigate the effect of a combination of salicylic acid at 2% w/w and sodium nitrite at 2% w/w in 9 patient volunteers with microbiologically proven fungal infection of the feet, application of the treatment produced a microbiological cure in all but one patient after 2 weeks of therapy. The symptom score (derived from a scoring system which measures erythema, vesicles, pustules, desquamation, encrustation and pruritus) decreased from a mean of 7 before treatment to a mean of 2 following treatment.

EXAMPLE 6

Investigation of the use of nitrate or nitrite administered topically in the mouth in the form of toothpaste, mouthwash or other orally acceptable vehicle to reduce the number of caries-producing organisms in dental plaque and to treat to prevent infection with *C albicans* or other harmful organisms showed such application to be effective.

The observation that oxides of nitrogen produced non-enzymatically from nitrite under conditions simulating those in the stomach kills *C albicans* and *E coli* extends these observations to the intestinal tract. *E coli* is closely related to Salmonella, Shigella and other pathogenic enterobacteria; all important causes of gastroenteritis in the mammal.

These results provide a rationale for active secretion of nitrate by the salivary glands. Nitrate itself is a innocuous precursor which only produces microbiocidal species when converted to nitrite and subjected to acid conditions. It is possible that Lactobacilli sp. transiently produce sufficient acid in the mouth after a carbohydrate meal to control the growth of oral pathogens but clearly a moderate intake of nitrate may be a desirable prerequisite in any contaminated environment despite any potential as a precursor of nitrosamines.

Further the production of intestinal nitrogen oxides may be inadequate if the oral flora which convert nitrate to nitrite are suppressed following therapy with broad-spectrum antibiotics. Similarly if gastric acid production is reduced, or if nitrate intake, which is largely dependent on leafy vegetables, is low this protective mechanism will be impaired. These are precisely the situations which predispose to oral and intestinal infections.

Whereas the foregoing study has concentrated on *C albicans* and *E coli* and the other organisms mentioned, it may also be important for providing protection from other serious gut pathogens which when swallowed may cause duodenal ulceration, for example *Helicobacter pylori*, amoebic dysentery and chronic intestinal parasitism. Accordingly the invention provides a dosage form for the treatment of bacterial, viral or fungal conditions, a method of sterilising an object, and a composition therefor.

The above also suggests an inexpensive and simple means of prevention of gastroenteritis in farmed pigs by modification of dietary nitrate intake without the use of antibiotics.

EXAMPLE 7

32 subjects with recalcitrant viral warts were treated with varying formulations of sodium nitrite acidified with the acid specified. The exact formulations are given in Table 1. All 32 patients had failed to respond to conventional topical wart applications and at least two treatments with liquid nitrogen. 12 subjects had plantar warts, 12 hand warts, 5 subungal or peri-ungal and 1 plane of the warts of the hand, 1 perianal and 1 lip wart.

Figure 5:
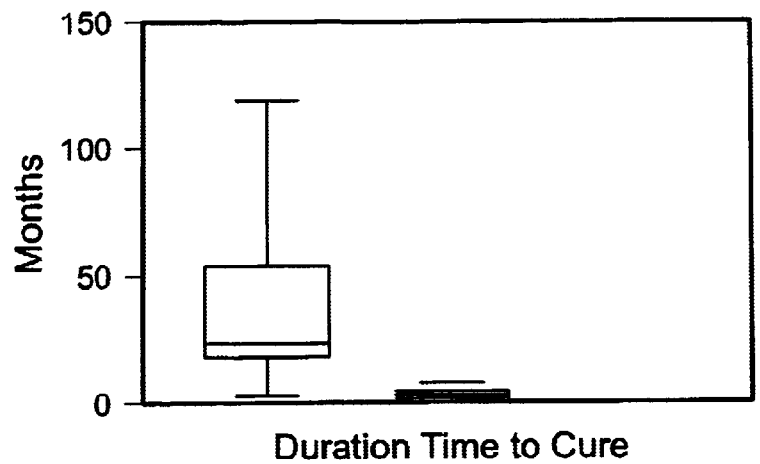
FIG. 5 shows a graph of the duration of the warts compared to the time for wart disappearance with the formulations given in Example 7, where n=32.

The warts had a duration with median 24 months this implies that the patients had a low chance of spontaneous improvement (See FIG. 5).

| Acid | Nitrite | No. of patients treated |
|---|---|---|
| Salicylic 5% cream | Sodium nitrite 5% cream | 5 |
| Ascorbic acid 5% cream | Sodium nitrite 5% cream | 7 |
| Ascorbic acid 10% cream | Sodium nitrite 10% cream | 2 |
| Salicylic acid 23% in alcohol based wart paint | Sodium nitrite 10% + copper acetate 0.5% | 9 |
| Salicylic acid 23% in alcohol based wart paint | Sodium nitrite 10% cream | 3 |
| Salicylic acid 23% in alcohol based wart paint | Sodium nitrite 15% solution | 6 |

The warts were prepared by scraping or abrading the skin to remove the dead skin then the sodium nitrite containing formulation was applied before applying the selected acidifying agent. The warts were treated every night and every three days the warts were rescrapped or abraded.

Figure 6:
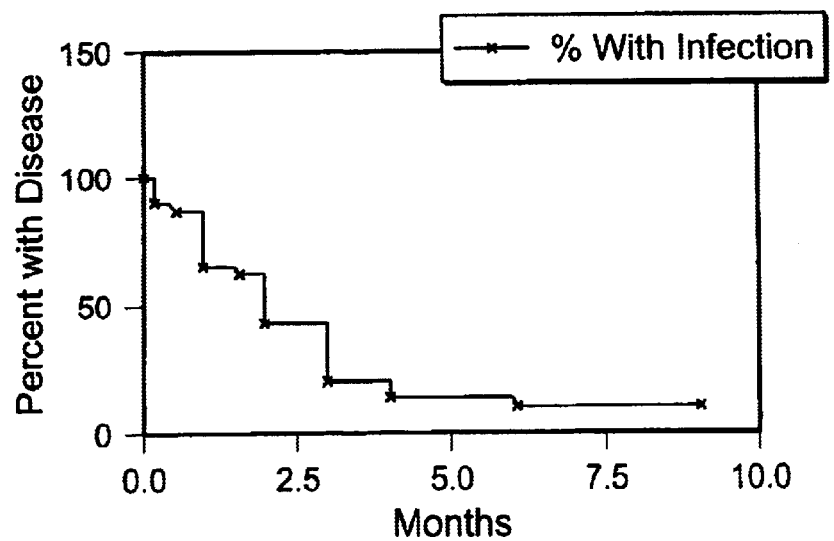
FIG. 6 shows the outcome of the treatment of patients with warts as a function of time, where n=32.

Clearance of the warts occurred with a median duration of 2 months regardless of the formulation of the treatment (see FIGS. 5 and 6). Copper was included to catalyze the release of nitrogen oxides from glutathione and proteins that had become nitrosated to extend the release of nitrogen oxides.

Four treatment failures were seen; three of these in patients who were being treated with immunosuppressive drug therapy for Lupus erthematosus, kidney transplant and dermatomyositis. Accordingly there was an 88% cure rate in all the subjects and a 96% cure rate if the immunosuppressed patients were excluded. Existing treatments such as using liquid nitrogen or salicylic acid paints result in 50–80% clearance.

EXAMPLE 8

30 patients with molluscum contagiosum lesions took part in a double blind trial. They were randomly treated with either 5% sodium nitrite co-applied with 5% salicylic acid under occlusion or 5% sodium nitrite without acidification. The mean age of the subjects was 7 years (with one outlier of 47 not included in the mean). The infection had a mean duration of 8.23+3.959 months. No significant difference was found in the number of lesions per patient or the number of times treatment was applied in the two groups.

In the case of co-application the sodium nitrate was applied to the skin with a cotton bud and then a fresh cotton bud was used to apply the salicylic acid. In the case of the sole application of sodium nitrite it was applied with a cotton bud. In both cases, if possible, the area was covered with "cling-film" or Sellotape.

As seen in Table 2 in the group treated with the active treatment 70% of the patients were cured and 28% of those in the control group were cured. The mean time to cure was 1.83+0.91 months

TABLE 2

| Treatment | Cured | Not cured |
|---|---|---|
| Acid and Nitrite | 12 | 4 |
| Control | 4 | 10 |

Kaplan Meier plots were performed for active and control patients (FIG. 7) and analyzed by the Logrank test which showed a significant difference in the survival curves with cure being greater in the active group (p=0.0183).

EXAMPLE 9

12 volunteers with no current or recent history of skin disease and taking no mediation randomly applied either low dose (0.5% nitrite) or high dose (5% nitrite) of a nitrogen oxide complex to their skin.

Subjects applied 2% w/w ascorbic acid in aqueous cream to a control site and an active site. Either the low dose or the high does nitrite cream was also applied to the active site. The creams were applied 3 times daily at 8 hourly intervals and both the control and the active sites were then occluded with an adhesive polythene/plastic dressing.

The last application of the cream was made 5 hours before the assessment of the reaction to allow the immediate vasodilatory effects of the nitrogen oxide complex to subside, so measuring only residual inflammation.

The thickness of the control and active sites were measured using a 'Mitotoyu' spring thickness gauge and redness was measured using reflectance erythema meter. Two 4 mm punch biopsies were taken from the active and control sites; one for formalin fixation for histological assessment, mass cell stains, neutrophil elastase and in situ nick end labelling and the other for snap freezing and OCT embedding for the other immunohistochemical stains.

Immunohistochemical was performed using a streptavidin biotin method and DAB detection with the antibodies in Table 3 and using ApopTag Plus in situ nick end labelling detection kit to identify apoptotic cells.

Staining was quantified by computerized image analysis and data analyzed by Wilcoxon's test for paired samples and Kruskal-Wallis' test for non-parametric analysis of variance in the multiple independent samples analyzed for effects of dose and duration (see Tables 4,5 and 6).

TABLE 3

| Epitope | Titre | Cells Stained |
|---|---|---|
| CD1a | 0.0451388889 | Langerhans cells |
| CD3 | 0.555555556 | pan-T cell |

TABLE 3-continued

| Epitope | Titre | Cells Stained |
| --- | --- | --- |
| CD4 | 1:150 | T-helper cells |
| CD8 | 0.555555556 | T-cells suppressor/cytotoxic |
| CD54 | 1:100 | ICAM-1 |
| CD6 | 0.0486111111 | Macrophages |
| CD106 | 1:100 | VCAM-1 |
| p53 | 0.0763888889 | Wild type p53 protein |
| Nitrosotyrosine* | 1:100 | Nitrosated tyrosine |
| Neutrophil elastase | 1:100 | Neutrophils |
| ApopTag** | Manufacturers instructions | Apoptotic cells |

*polyclonal, all other antibodies monoclonal
**based on in situ detection of cleaved DNA with peroxidase 5 visualization.

The reflectance erythema measurement of the nitrogen oxide complex treated sites was 32.25±5.46 (mean+sd) significantly higher than the control sites 18.08±5.81 (p=0.0022, Wilcoxon's) Skin fold thickness was 5.04±0.75 mm in the nitrogen oxide complex treated patches which was significantly greater than that of control skin 3.25±0.54 (p=0.0022, Wilcoxon's). These measures were not significantly influenced by dose or duration of exposure, except there was a trend for greater skin fold thickness in the high dose group (5.4 mm±0.21 vs 4.7 mm±0.32) (p=0.075).

Histology of all actively treated sites showed a significant increase in oedema, endothelial swelling, cloudy swelling of keratinocytes, and a mixed infiltrate of lymphocytes and neutrophils. These changes were quantified on a 0–4 ordinal scale and were similar in low does, high dose, short exposure and long exposure. The number of mast cells seen in Azure A stained sections was similar in control and nitrogen oxide complex treated skin.

A cytotoxic effect was seen in all keratinocytes which was manifest as cloudy swelling. When extensive this leads to the formation of bullae high in the epidermis filled with acute inflammatory cells and cells which have undergone cytotoxic changes with constriction of the nucleus and cloudy swelling of clear cytoplasm around them. Only a minority of these degenerate cells had undergone apoptosis as judged by staining with ApopTag. Within the viable epidermis, there was also an increase in apoptotic cells. This suggests that normal keratinocytes, not virally infected and relatively resistant to the well known apoptotic effects of nitric oxide. Apoptotic cells were also detected in the dermis, particularly around adnexal structures. The positive nitrosotyrosine staining around sebaceous glands suggests that the nitrogen oxide complex was preferentially absorbed through follicles.

Nitrogen oxide complex treated skin showed significant increases in immuno-competent cells expressing CD3, CD8, CD68 and neutrophil elastase and in the adhesion molecules which attract trafficking of the cells to the site, ICAM-1 and VCAM-1. The presence of nitrosotyrosine staining in these cells is indicative of the formation of peroxynitrite (ONOO-) and of p53 which indicates that part of the effect of the complex is mediated through toxicity towards DNA in these cells. In healthy skin nitrogen oxide complex did cause some apoptosis but this was surprisingly small at the doses used and we postulate that the effect is likely to be in infected cells. The antigen processing cells of the skin (CD1a positive) were seen to lose dendricity and drop from the epidermis so there were significantly fewer in the treated skin. As these cells behave in this way when activated and functioning to process a newly recognized antigen, this would seem to offer further evidence for an immunopotentiating role for the nitrogen oxide complex. Ki-67 staining for dividing cells did not differ in control or active sites. This would suggest that in warts, for example, the action is not one of reducing cell proliferation. Kruskal-Walls test was used to test the effects of time or duration of nitrogen oxide complex treatment on clinical and immunohistochemical response. The effect of the dosage on the skins reaction is given in Table 5. There were fewer CD4 positive cells in the high dose than the low dose group, and likewise with CD68 positive cells. Although Ki-67 positive cells were not significantly different between the control site and the nitrogen oxide complex treated site, there was a significant increase with high dose compared with low dose.

After 24 and 48 hours exposure to the nitrogen oxide complex the extent of apoptosis was measured, see Table 6. There was significantly greater apoptosis after 48 hours than after 24 hours. The CD4 positive cells count rose significantly after 48 hours compared to after 12 hours. The difference for p53 was not quite statistically significant. Similarly, cloudy swelling tended to be greater in the longer duration treatment but was not statistically significant.

TABLE 4

|  | Nitrogen Oxide Complex | | Control | | Significance Wilcoxon's |
| --- | --- | --- | --- | --- | --- |
|  | Mean | S.D. | Mean | S.D. | Test |
| ApopTag | 12.5 | 10.1 | 0.41 | 1.6 | 0.0033 |
| Ki67 | 6.82 | 3.82 | 6.62 | 2.854 | 0.67 |
| CD1a* | 0.86 | 0.69 | 3.43 | 0.53 | 0.022 |
| CD3 | 574.7 | 396.3 | 216.1 | 122.1 | 0.0186 |
| CD4 | 608.2 | 458.2 | 176.3 | 149.9 | 0.0125 |
| CD8 | 275.7 | 193.1 | 122.1 | 106.1 | 0.0284 |
| CD68 | 673.1 | 542.4 | 301.4 | 361.3 | 0.0044 |
| Nitrosotyrosine* | 3.4 | 0.7 | 0.9 | 1.1 | 0.043 |
| p53 | 214.4 | 266.4 | 22.08 | 53.8 | 0.0029 |
| Neutrophils | 569.4 | 385.9 | 71 | 113.1 | 0.043 |
| ICAM-1 | 705.9 | 704.5 | 201.9 | 160.9 | 0.0209 |
| VCAM-1 | 1.5 | 1.17 | 0.5 | 0.9 | 0.0357 |

*Where cell counting was difficult e.g. more diffuse staining/dendritic cells, staining was graded subjectively on a scale of 0–4.

Ki67 was counted in the epidermis and ApopTag positive cells counted per standard section through a 3 mm punch biopsy. All other counts were done by computerized image analysis on a fixed standard measuring frame and are expressed as cells per mm2.

TABLE 5

|  | High Dose (cells/mm2) | | Low Dose (cells/mm2) | | Kruskal-Wallis Test |
| --- | --- | --- | --- | --- | --- |
|  | Mean | S.D. | Mean | S.D. |  |
| Ki67 | 152 | 35.2 | 73.6 | 8 | 0.01 |
| CD4 | 280 | 78.4 | 936 | 185.6 | 0.02 |
| CD68 | 379.2 | 65.6 | 916.8 | 262.4 | 0.04 |

TABLE 6

|  | 12/24* hrs | | 48 hrs | | Kruskal-Wallis Test |
| --- | --- | --- | --- | --- | --- |
|  | Mean | S.D. | Mean | S.D. |  |
| ApopTag* | 3.5 | 1.82 | 14.16 | 2.56 | <0.005 |
| CD4 | 285.9 | 193.6 | 824 | 193.6 | 0.05 |

TABLE 6-continued

|  | 12/24* hrs | | 48 hrs | | Kruskal- |
| --- | --- | --- | --- | --- | --- |
|  | Mean | S.D. | Mean | S.D. | Wallis Test |
| Cloudy swelling** | 1.7 | 0.33 | 2.5 | 0.224 | 0.07 |
| p53 | 70.1 | 47.04 | 335.2 | 125.7 | 0.07 |

Ki67 was counted in the epidermis and Apoptag positive cells counted per standard section through a 3 mm punch biopsy. All other counts were done by comperized image analysis on a fixed standard measuring frame and are expressed as cells per mm2.
**Where cell counting was difficult e.g. more diffuse staining/dendritic cells, staining was graded subjectively on a scale of 0–4.

The nitrogen oxide complexes of the invention may be formed by a combination of ascorbic acid and nitrite on the skin, which causes the release of nitrogen oxides, inter alia nitric oxide, nitrous oxide, nitrogen dioxide and dinitrogen trioxide. The increase in T helper cells and macrophages was greater in low dose subjects and suggests that at lower doses nitrogen oxides can be pro-inflammatory but at higher doses becomes cytotoxic to the immunocompetent cells and begins to exert an inhibitory effect. The nitrogen oxide complex led to a marked induction of ICAM-1 and a moderate increase in VCAM-1 expression. The pattern of inflammation was unusual in showing a marked infiltrate of macrophages after only 24 hours, so showing that activated macrophages use nitrogen oxides to specifically attract more macrophages to kill a pathogen.

The promotion of apotosis and recruitment of all the immunocompetent cells required for effective recognition of a pathogen by the immune system of a host, results from application of a preparation of a combination of nitrite or precursor of nitrogen oxides and an acidifying agent. Accordingly, these findings support a potential immunopotentiating effect of the combination of nitrite or other precursor of nitrogen oxides such as NO or $NO_2$ and a acidifying agent.

EXAMPLE 10

A two part component delivery system was made up. Each component was in the form of a wax stick which can be rubbed onto an effective area at regular intervals in accordance with a physician's instructions.

The two components were made up as follows:
10% ASCORBYL PALMITATE
Component
  Ascorbyl Palmitate 10%
  White Soft Paraffin 25
  Light Liquid Paraffin 20
  Hard Paraffin 20
  Arlacel 165 15
  Cetosteryl Alcohol 10
Method
  1. Weigh all the components into a vessel.
  2. Heat the vessel and stir the mixture until all the components have melted and the mixture is homogenous.
  3. Pour the molten wax into jars and allow to cool to room temperature.

| 10% SODIUM NITRITE WAX | |
| --- | --- |
| Components | |
| Phase A | |
| Light Liquid Paraffin | 7.5% |
| White Soft Paraffin | 20 |
| Arlacel 582 | 10 |
| Cetosteryl alcohol | 10 |
| Phenoxyethanol | 1 |
| Phase B | |
| Sodium Nitrite | 10 |
| Purified Water | 20 |

Method
  1. Weigh the Phase A components into a vessel, heat to 70° C. and stir until homogenous.
  2. Weigh the Phase B components into another vessel heat to 70° C. and stir, ensure that all the sodium nitrite has dissolved.
  3. When both phases have reach 70° C., add phase A to phase B and homogenize for 5 minutes.
  4. Pour the molten wax into jars and allow to cool to room temperature.

As is shown from FIG. 8, the use of this admixture tends to release a substantial excess of NO from the two-part delivery system. This is possibly because NO is a small molecule which results in a more effective treatment of viral skin diseases.

What we claim is:

1. A method of treating a microbial infection on a human or animal subject, the method comprising:
   mixing an effective amount of a pharmaceutically acceptable acidifying agent with a component, the component being selected from the group consisting of alkali metal nitrites and alkaline earth metal nitrites, and the acidifying agent being selected from the group consisting of ascorbyl palmitate, salicylic acid, lactic acid, citric acid, formic acid, benzoic acid and tartaric acid; and
   applying the composition to an area of the subject where the microbial infection is located,
   with the proviso that the composition contains only one acidifying agent, and, upon mixing the acidifying agent and the component, the acidifying agent is present in an amount so that a pH of the mixture is less than 4.

2. The method of claim 1, wherein the pharmaceutically acceptable acidifying agent and the component are mixed at the area of the subject where the microbial infection is located.

3. The method of claim 1, wherein the pharmaceutically acceptable acidifying agent and the component are mixed before reaching the area of the subject where the microbial infection is located.

4. The method of claim 1, wherein the microbial infection is selected from the group consisting of a bacterial infection, a viral infection, a fungal infection, and a parasitic infection.

5. The method of claim 1, wherein the microbial infection comprises a viral infection.

6. The method of claim 5, wherein the viral infection is caused by infection from a virus selected from the group consisting of molluscum contagiosum, herpes simplex type 1, herpes simplex type 2, varicella zoster, vaccinia and papilloma.

7. The method of claim 1, wherein the microbial infection comprises a bacterial infection.

8. The method of claim 7, wherein the bacterial infection is caused by an organism selected from the group consisting of Staphylococcus sp., Francisella sp., Mycobacterium sp., E. coli and Helicobacter pylon.

9. The method of claim 1, wherein the microbial infection comprises a fungal infection.

10. The method of claim 9, wherein the fungal infection is caused by an organism selected from the group consisting of C. Albicans and organisms capable of causing the condition Tinea Pedis.

11. The method of claim 1, wherein the microbial infection comprises a parasitic infection.

12. The method of claim 11, wherein the parasitic infection is selected from the group consisting of Leishmania sp. and organisms capable of causing amoebic dysentery.

13. The method of claim 1, wherein the component and the pharmaceutically acceptable acidifying agent are kept separate prior to mixing.

14. The method of claim 1, further comprising reacting the component with the pharmaceutically acceptable acidifying agent to form a compound selected from the group consisting of NO, $NO_2$, $N_2O$ and $N_2O_3$.

15. The method of claim 1, further comprising reacting the component with the pharmaceutically acceptable acidifying agent to form a compound selected from the group consisting of NO and $NO_2$.

16. The method of claim 1, wherein the pharmaceutically acceptable acidifying agent comprises an organic acid.

17. The method of claim 1, wherein the pharmaceutically acceptable acidifying agent is salicyhic acid, and the mixture of the pharmaceutically acceptable acidifying agent and the component at the area of the subject where the microbial infection is located comprises from 0.5% to 30% by weight salicylic acid and from 0.5% to 30% by weight of the component.

18. The method of claim 1, wherein the pharmaceutically acceptable acidifying agent is citric acid, the mixture of the pharmaceutically acceptable acidifying agent and the component at the area of the subject where the microbial infection is located comprises from 0.5% to 45% by weight citric acid and from 0.5% to 30% by weight of the component.

19. The method of claim 1, wherein the pharmaceutically acceptable acidifying agent is ascorbyl palmitate, the mixture of the pharmaceutically acceptable acidifying agent and the component at the area of the subject where the microbial infection is located comprises from 3% to 25% by weight ascorbyl palmitate and from 0.5% to 30% by weight of the component.

20. The method of claim 1, wherein the pharmaceutically acceptable acidifying agent is lactic acid, the mixture of the pharmaceutically acceptable acidifying agent and the component at the area of the subject where the microbial infection is located comprises from 0.5% to 20% by weight lactic acid and from 0.5% to 30% by weight of the component.

21. The method of claim 1, wherein the pharmaceutically acceptable acidifying agent is formic acid, the mixture of the pharmaceutically acceptable acidifying agent and the component at the area of the subject where the microbial infection is located comprises from 0.5% to 20% by weight formic acid and from 0.5% to 30% by weight of the component.

22. The method of claim 1, wherein the pharmaceutically acceptable acidifying agent is benzoic acid, the mixture of the pharmaceutically acceptable acidifying agent and the component at the area of the subject where the microbial infection is located comprises from 0.5% to 20% by weight benzoic acid and from 0.5% to 30% by weight of the component.

23. The method of claim 1, wherein the pharmaceutically acceptable acidifying agent is tartaric acid, the mixture of the pharmaceutically acceptable acidifying agent and the component at the area of the subject where the microbial infection is located comprises from 0.5% to 20% by weight tartaric acid and from 0.5% to 30% by weight of the component.

24. The method of claim 1, wherein the component has a first pharmaceutically acceptable carrier and the pharmaceutically acceptable acidifying agent has a second pharmaceutically acceptable carrier.

25. The method of claim 1, wherein, upon mixing the pharmaceutically acceptable agent and the component, the pharmaceutically acceptable acidifying agent is present in an amount so that a pH of the mixture is less than 3.

26. The method of claim 1, wherein, upon mixing the pharmaceutically acceptable agent and the component, the pharmaceutically acceptable acidifying agent is present in an amount so that a pH of the mixture is less than 2.

27. The method of claim 1, wherein the pharmaceutically acceptable acidifying agent is ascorbyl palmitate.

* * * * *